United States Patent
Lavoie

(10) Patent No.: US 11,083,395 B2
(45) Date of Patent: Aug. 10, 2021

(54) METHOD AND SYSTEM FOR THE VISUAL REPRESENTATION OF THE KINEMATICS OF A PATIENT'S JOINT AND ASSOCIATED PARAMETERS

(71) Applicant: EIFFEL MEDTECH INC., Montréal (CA)

(72) Inventor: Frédéric Lavoie, Ste-Martine (CA)

(73) Assignee: Eiffel Medtech Inc., Montreal (CA)

( * ) Notice: Subject to any disclaimer, the term of this patent is extended or adjusted under 35 U.S.C. 154(b) by 892 days.

(21) Appl. No.: 15/111,122

(22) PCT Filed: Jan. 13, 2015

(86) PCT No.: PCT/CA2015/000073
§ 371 (c)(1),
(2) Date: Jul. 12, 2016

(87) PCT Pub. No.: WO2015/103699
PCT Pub. Date: Jul. 16, 2015

(65) Prior Publication Data
US 2016/0331281 A1     Nov. 17, 2016

Related U.S. Application Data

(60) Provisional application No. 61/926,736, filed on Jan. 13, 2014.

(51) Int. Cl.
*A61B 5/05*     (2021.01)
*A61B 5/11*     (2006.01)
(Continued)

(52) U.S. Cl.
CPC .......... *A61B 5/1122* (2013.01); *A61B 5/055* (2013.01); *A61B 5/1114* (2013.01); *A61B 5/4585* (2013.01); *A61B 5/7282* (2013.01); *A61B 5/743* (2013.01); *A61B 6/032* (2013.01); *A61B 6/463* (2013.01); *A61B 6/466* (2013.01);
(Continued)

(58) Field of Classification Search
CPC combination set(s) only.
See application file for complete search history.

(56) References Cited

U.S. PATENT DOCUMENTS

| | | | | |
|---|---|---|---|---|
| 6,161,080 | A * | 12/2000 | Aouni-Ateshian | G16H 50/50 703/11 |
| 2004/0167390 | A1* | 8/2004 | Alexander | A61B 5/055 600/410 |
| 2013/0185310 | A1* | 7/2013 | De Guise | G06F 19/324 707/748 |

OTHER PUBLICATIONS

Roetenberg etal (Xsens MVN: Full 6DOF human motion tracking using miniature inertial sensors) (Year: 2013).*

* cited by examiner

*Primary Examiner* — Joel F Brutus
(74) *Attorney, Agent, or Firm* — PRAXIS

(57) ABSTRACT

There is provided a method and system for visually representing the kinematics of a patient's joint in real-time. The method comprises the steps of receiving characteristics of a measured movement of the joint, computing at least one kinematic object vector using specific morphology of the Joint structures and the characteristics of the measured movement of the joint, displaying a 3D representation of the joint structures based on the specific morphology of the joint structures and on the characteristics of measured movement of the joint, linking the at least one kinematic object vector with the joint structures and dynamically displaying the at least one kinematic object vector superimposed on the 3D representation of the joint structures.

14 Claims, 3 Drawing Sheets

(51) Int. Cl.
*A61B 8/08* (2006.01)
*A61B 8/00* (2006.01)
*A61B 5/00* (2006.01)
*A61B 5/055* (2006.01)
*A61B 6/03* (2006.01)
*A61B 6/00* (2006.01)

(52) U.S. Cl.
CPC ............ *A61B 6/505* (2013.01); *A61B 6/5217* (2013.01); *A61B 8/0841* (2013.01); *A61B 8/0875* (2013.01); *A61B 8/463* (2013.01); *A61B 8/466* (2013.01); *A61B 8/5223* (2013.01); *A61B 6/5247* (2013.01); *A61B 8/5246* (2013.01); *A61B 8/5261* (2013.01)

METHOD AND SYSTEM FOR THE VISUAL REPRESENTATION OF THE KINEMATICS OF A PATIENT'S JOINT AND ASSOCIATED PARAMETERS

CROSS-REFERENCE TO RELATED APPLICATIONS

This application claims the benefits of U.S. provisional patent application No. 61/926,736 filed on Jan. 13, 2014, which is herein incorporated by reference.

TECHNICAL FIELD

The present disclosure relates to a method and system for the visual representation of the kinematics of a patient's joint and associated parameters.

BACKGROUND

Assessment of a joint's motion and applied forces, or kinematics and kinetics respectively, can help diagnose articular injury and guide the treatment of the injury. For that purpose, however, articular motion and forces need to be measured in a reproducible fashion. Also, the three-dimensional movement and forces are often split in components that are relevant to the anatomy and function of each specific joint to relate the data to the framework used by clinicians. 3D motion and forces are split in components by determining an axis system, or referential, for the bones articulating together (e.g. the femur and the tibia for the knee joint), knowing that even a little modification of the location of an axis system can significantly alter the way kinematics are decomposed, the so-called crosstalk phenomenon.

Relative motion of the bones forming a joint can also be analyzed using the instantaneous helical axis method, which represents motion as a single rotation axis and a translation along that axis for each studied time interval. This method is not easy to interpret clinically if it is not related to the anatomical structures, also it makes it difficult to assess motion components of smaller amplitude as they are overwhelmed by other components of larger amplitude (e.g. tibial internal and external rotation relative to flexion); therefore kinematics are usually split using referentials.

Once 3D motion is split according to referentials, up to three values of rotation and three values of translation are obtained for each time interval that is considered for the kinematic analysis; therefore, if the relative position of the bones forming the joint is measured at a rate of 60 Hz (a common sampling rate of motion tracking systems), 360 numerical values per second of kinematic recording are obtained. The same principle applies to force measurements.

2D graphs are used to visualize the kinematics data (e.g. KneeKG™) and/or kinetics data but require the reader to understand the graphs and combine them mentally to get a sense of how the joint is moving and forces are applied.

Therefore, there is a need for a real-time graphic representation of articular motion and forces and visualization of their spatial relationship with the anatomical structures for a better understanding of joint kinetics and kinematics.

SUMMARY

The present disclosure provides a method for visually representing the kinematics of a patient's joint in real-time, the method comprising:

receiving characteristics of a measured movement of the joint;

computing at least one kinematic object vector using specific morphology of the joint structures and the characteristics of the measured movement of the joint;

displaying a 3D representation of the joint structures based on the specific morphology of the joint structures and on the characteristics of measured movement of the joint;

linking the at least one kinematic object vector with the joint structures; and dynamically displaying the at least one kinematic object vector superimposed on the 3D representation of the joint structures.

The present disclosure also provides a system for visually representing the kinematics of a patient's joint in real-time, the method comprising:

an input/output interface configured to receive characteristics of a measured movement of the joint;

a display;

a processor in communication with the input/output interface and the display, the processor being configured so as to:
    compute at least one kinematic object vector using specific morphology of the joint structures and the characteristics of the measured movement of the joint;
    provide to the display a 3D representation of the joint structures based on the specific morphology of the joint structures and on the characteristics of measured movement of the joint;
    link the at least one kinematic object vector with the joint structures; and
    dynamically provide to the display the at least one kinematic object vector to be superimposed on the 3D representation of the joint structures.

The present disclosure further provides a method and system as described above wherein the at least one kinematic object vector is represented by a visual indicator having a shape, position, orientation, size and color representative of characteristics of the measured movement of the joint; the characteristics of the measured movement of the joint being selected from the group consisting of linear displacement, angular displacement, articular contact points, velocity, acceleration and rotation center.

BRIEF DESCRIPTION OF THE FIGURES

Embodiments of the disclosure will be described by way of examples only with reference to the accompanying drawing, in which.

Figure 1:
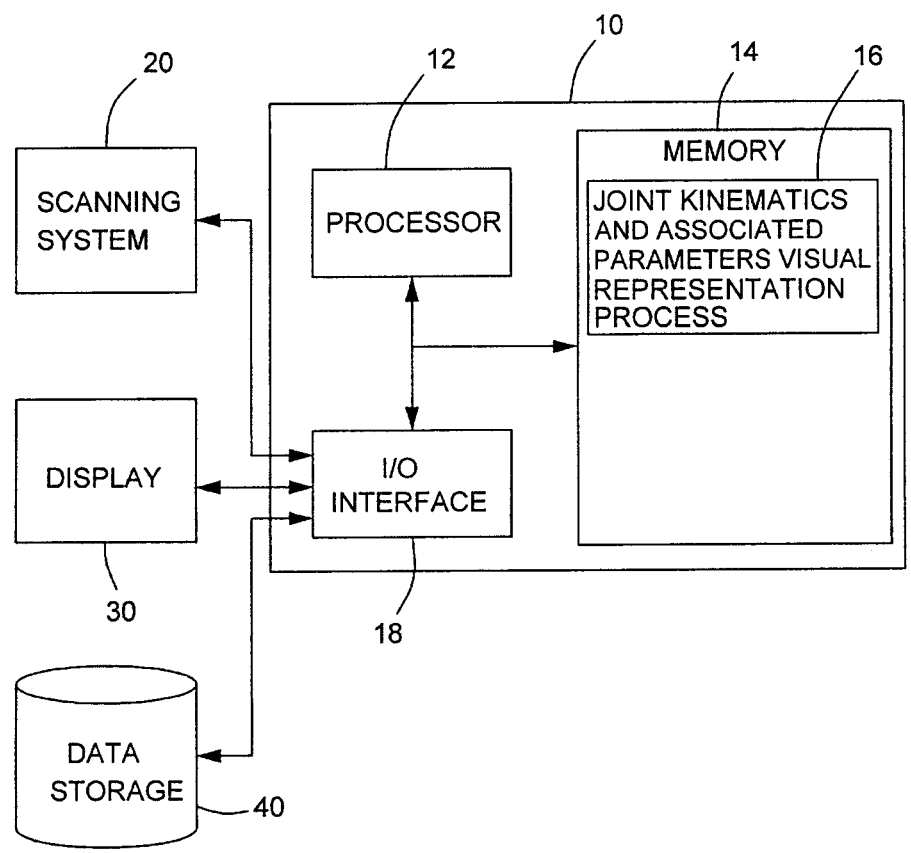
FIG. 1 is a schematic representation of a joint kinematics and associated parameters visual representation system in accordance with an illustrative embodiment of the present disclosure.

Similar references used in different Figures denote similar components.

DETAILED DESCRIPTION

Generally stated, the non-limitative illustrative embodiments of the present disclosure provide a method and system for the visual representation of the kinematics of a patient's joint and associated parameters, amongst which forces and moments. The kinematics of the patient's joint are visually represented in 3D along with indicators showing a number of associated parameters such as, for example, amplitude, orientation, linear and/or angular components, velocity, acceleration, axes of rotation, rotational and/or translational vectors and articular contact points, etc., the 3D representation being in spatial relationship in a virtual 3D rendering with representations of the various structures for which movement is and forces are measured. The visual representation may also show the uncertainty of the displayed parameters.

The 3D representation of each specific bone is displayed in real time in the virtual environment visualization, the position and orientation of the bones being determined by a calibration procedure and continually refreshed with the displacements of the positional sensors affixed to the bones. Joint movement, i.e. the relative movements of the bones forming the joint, are construed in accordance with reproducible and clinically relevant anatomical landmarks and displayed in real time in the virtual environment visualization and thus linking the movements and forces of the joint with the anatomical structures forming the joint. The visual representation of the joint movement, or one or more of its components, is displayed using "kinematic objects", i.e. amplitude, orientation, linear and/or angular components, velocity, acceleration, axes of rotation, rotational and/or translational vectors and articular contact points. These kinematic objects are dynamically displayed in the virtual environment visualization at the same time as the bones as they move, thus allowing the linking of the kinematics with the anatomical structure of the joint.

The shape, position, orientation, size and color of the kinematic objects are determined by the characteristics of the measured movement: linear displacement, angular displacement, articular contact points, velocity, acceleration and rotation center. Various display modes are available to analyze the displayed kinematics, for example the "kinematic drag" which displays the path of bone and/or kinematics and/or their intersection for a given time period. Another example of display mode is the display of the uncertainty.

Kinematic Object Vector Properties

The kinematic object vector is a dynamic curved vector displayed in the navigation volume in which the kinematic is measured;

The length of the vector is proportional to the total linear displacement;

The bend of the vector is proportional to the angular displacement with its center of rotation on the helical axis of the measured motion;

The transverse area of the vector is proportional to the acceleration and/or velocity;

The transverse shape of the vector can be changed dynamically according to the measured parameters (area divided between the parameters);

The vector is positioned in the plane normal to the helical axis of the measured movement;

The vector may represent the overall kinematics of the joint or only one or more of its components;

The vector is refreshed in real time;

The vector can be displayed in a kinematic drag mode.

The vector can be displayed with indicators of uncertainty for its various values.

Referring to FIG. 1, the joint kinematics and associated parameters visual representation system 10 includes a processor 12 with an associated memory 14 having stored therein processor executable instructions 16 for configuring the processor 12 to perform various processes, namely the joint kinematics and associated parameters visual representation process, which process will be further described below. The joint kinematics and associated parameters visual representation system 10 further includes an input/output (I/O) interface 18 for communication with a scanning system 20 and a display 30.

The display 30 may be, for example, a standard display screen, tablet, image overlay on real structures, augmented reality glasses (e.g. Google™ glasses).

The joint kinematics and associated parameters visual representation system 10 obtains, from the scanning system 20, real-time spatial coordinates of positional sensors secured to the bones located on either side of the joint and executes the joint kinematics and associated parameters visual representation process using the acquired data and 3D models of the specific morphology of the bones (cartilage included or not) constituting the joint whose motion is being measured and analyzed. The resulting 3D representation is then displayed on the display 30 and may be saved to the memory 14, to other data storage devices or medium 40, or provided to a further system via the I/O interface 18.

The scanning system 20 provides the joint kinematics and associated parameters visual representation system 10 with joint information, monitored in space and time, for the visual representation process in order to produce the 3D representation. The scanning system 20 includes motion capture capabilities (optical, electromagnetic, ultrasonic, etc.) with motion sensors to be positioned on the bones constituting the joint, as well as a registration procedure of the 3D models (navigated ultrasound and/or navigated palpation and/or joint mobilization).

Figure 2:
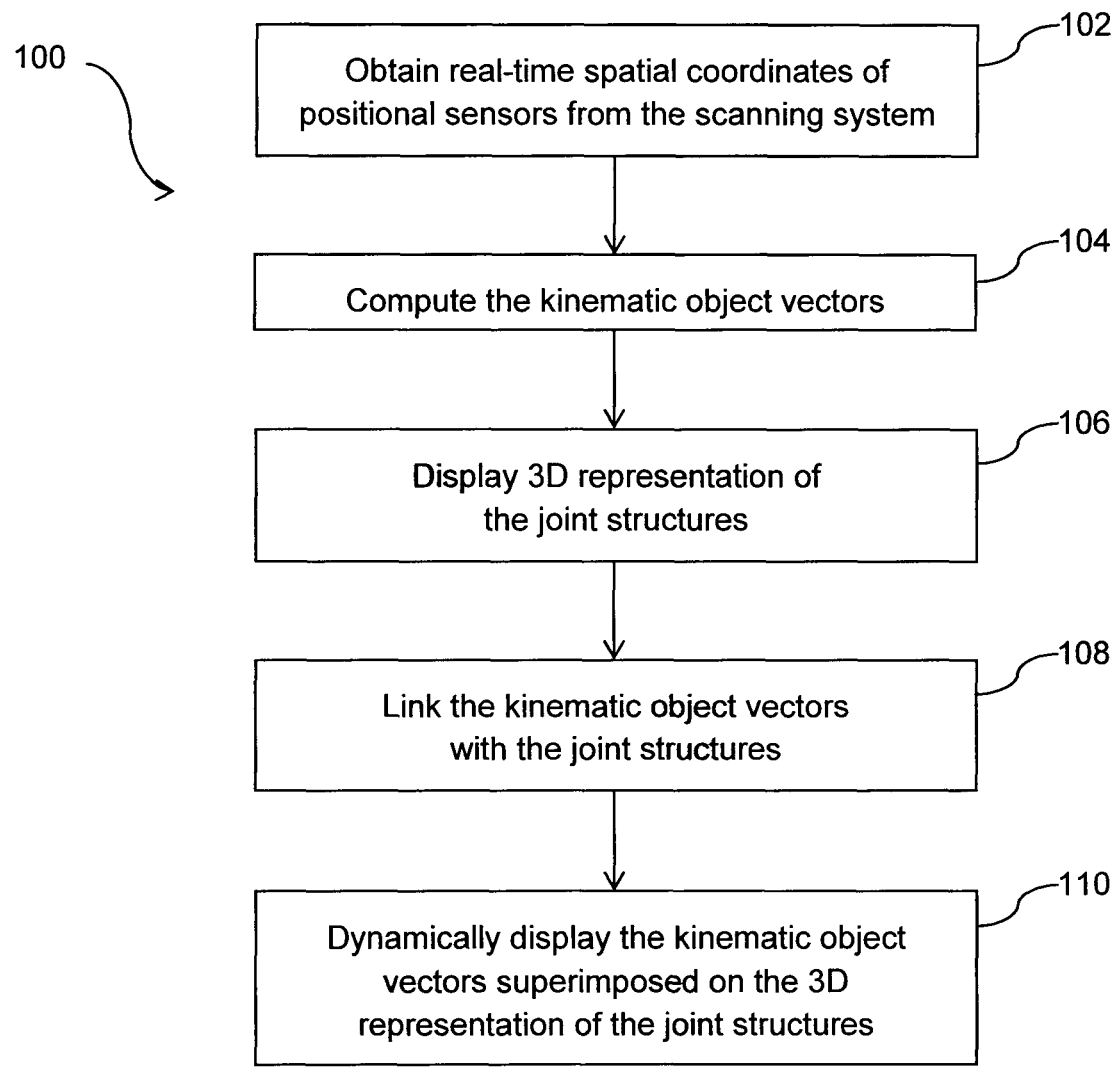
FIG. 2 is a flow diagram of a joint kinematics and associated parameters visual representation process in accordance with an illustrative embodiment of the present disclosure.

Referring to FIG. 2, there is shown a flow diagram of an illustrative example of the joint kinematics and associated parameters visual representation process 100 executed by the processor 12 of FIG. 1. Steps of the process 100 are indicated by blocks 102 to 110.

The process 100 starts at block 102 where the processor 12 obtains from the scanning system 20, real-time spatial coordinates of positional sensors secured to the bones located on either side of the joint.

Then, at block 104, the processor 12 computes the kinematic object vectors using the acquired data and 3D models of the specific morphology of the bones (cartilage included or not) constituting the joint whose motion is being measured and analyzed.

At block 106, a 3D representation of the joint structures is displayed on the display based on real-time spatial coordinates from the positional sensors.

Following this, at block 108, the kinematic object vectors are linked with the joint structures displayed at block 106 and, at block 110, the kinematic object vectors are dynamically displayed superimposed on the 3D representation of the joint structures.

The 3D models can be obtained in various ways: via computed tomography (CT), magnetic resonance imaging (MRI), reconstruction from 2D biplane images biplane, ultrasound images, etc.

The joint kinematics and associated parameters visual representation process 100 executed by the processor 12 determines the output format of the kinematics by defining the reference system (i.e. referential or axes system) used to reproducibly decompose the 3D motion into clinically relevant elements. It is then possible to view the joint movement as a whole via display 30 but most importantly it is also possible to reproducibly extract clinically relevant components of the movement in order to study them specifically in relation to various motor activities and/or joint pathologies.

The visual representation displays dynamic rotation axes (i.e. constantly refreshing during movement) and curved or straight vectors (i.e. arrows), also dynamic, whose characteristics (length, caliber, color, curvature, position) depend on the measured movement. The position and orientation of the vectors are associated with their respective axis of rotation. For example, in the case where the joint is the knee, the kinematics can be divided into flexion-extension (transverse axis coinciding with the center of curvature of the posterior femoral condyles) and internal-external tibial rotation (generally a longitudinal axis passing through the medial tibial plateau). The purpose of the proposed visual representation is to visualize in real time the position of the axes of movement and the characteristics of the movement in question (amplitude, velocity, and acceleration).

Figure 3:
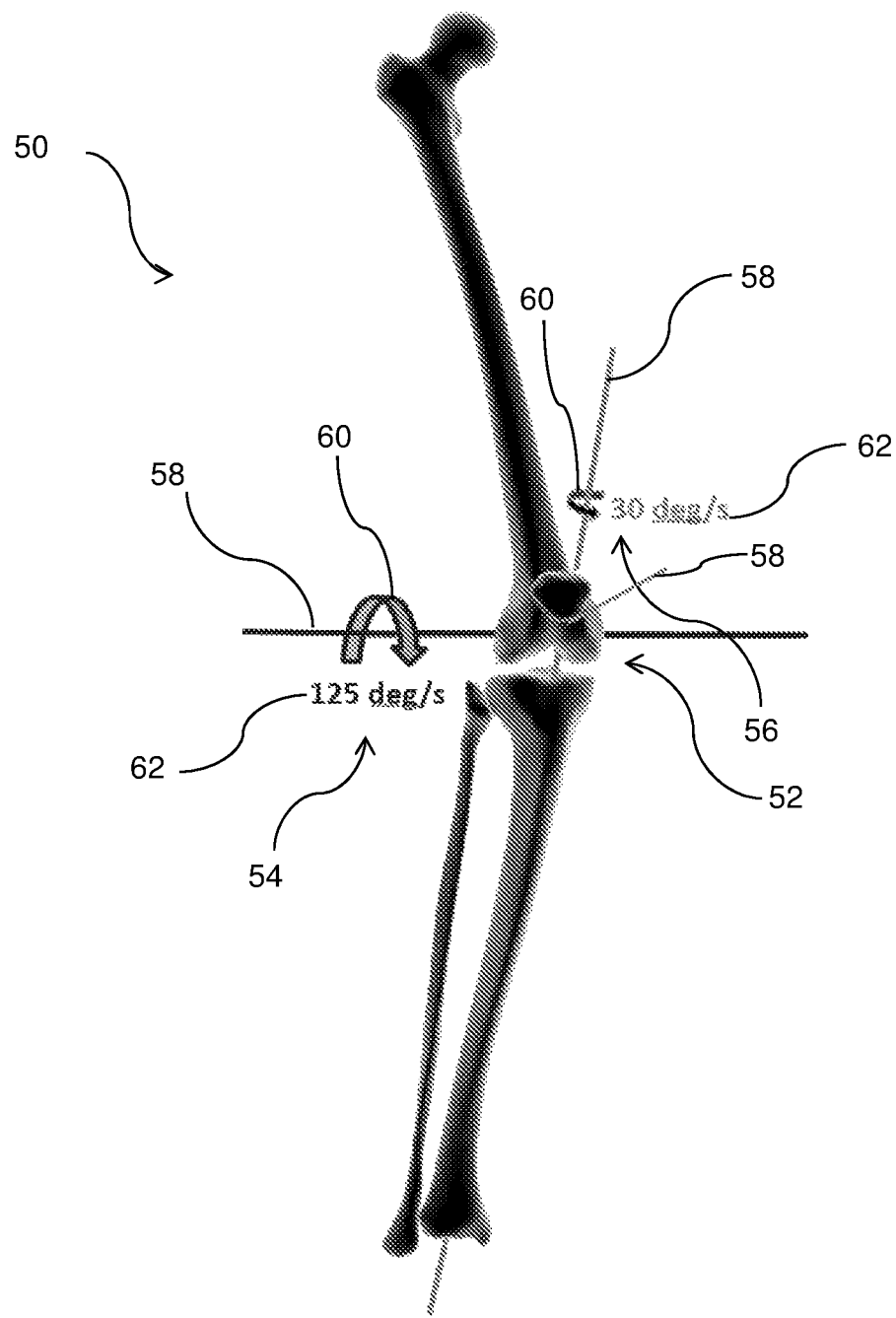
FIG. 3 is a schematic representation of a static capture of an example of a virtual environment visualization of joint kinematics and associated parameters for a human right knee.

Referring to FIG. 3, there is shown a schematic representation of a static capture of an example of a virtual environment visualization of joint kinematics and associated parameters for a human right knee 52. In this example, total motion is decomposed in two components (i.e. kinematic object vectors): a first kinematic object vector 54 visually represents rotation around an anatomy-based medio-lateral axis representing knee flexion and a second kinematic object vector 56 visually represents the remainder of motion with the helical axis method. Lines 58 represent the axes around which rotation occurs at that specific moment; the direction of the curved arrows 60 represent the direction of rotation; the size of the arrows 60 is proportional to angular velocity. Optionally, numerical values 62 may be displayed to quantify one of more parameters. It is to be understood that in use the various visual indicators 58, 60, 62, are designed to be dynamic and are updated in real-time. It is further to be understood that various other indicators may be used to represent associated parameters.

Although the present disclosure has been described with a certain degree of particularity and by way of illustrative embodiments and examples thereof, it is to be understood that the present disclosure is not limited to the features of the embodiments described and illustrated herein, but includes all variations and modifications within the scope and spirit of the disclosure as hereinafter claimed.

What is claimed is:

1. A method for visually representing the kinematics of a joint of a patient in real-time, the method comprising:
   receiving characteristics of a measured movement of the joint of the patient in real-time;
   computing at least one kinematic object vector using specific morphology of the joint structures and the characteristics of the measured movement of the joint of the patient in real-time;
   displaying a 3D representation of structures of the joint of the patient based on the specific morphology of the structures of the joint of the patient and on the characteristics of measured movement of the joint of the patient;
   linking the at least one kinematic object vector with the structures of the joint of the patient; and
   dynamically displaying the at least one kinematic object vector in the form of an arrow superimposed on the 3D representation of the structures of the joint of the patient in real-time.

2. A method in accordance with claim 1, wherein characteristics of the arrow are indicative of at least one parameter selected from the group consisting of an amplitude, an orientation, a linear component, an angular component, a velocity, an acceleration, an articular contact points, an axe of rotation a rotational vector and a translational vector.

3. A method in accordance with claim 1, wherein the characteristics of the arrow are further indicative of an uncertainty associated with the computing of the at least one kinematic object.

4. A method in accordance with claim 1, wherein the arrow is dynamically displayed in accordance with displacements of positional sensors affixed to joint structures.

5. A method in accordance with claim 1, wherein arrow has a length proportional to a total linear displacement, a bend proportional to an angular displacement and a transverse area proportional to an acceleration and/or velocity.

6. A method in accordance with claim 1, wherein the specific morphology of the structures of the joint of the patient is based on 3D models of the specific morphology of bones constituting the joint of the patient.

7. A method in accordance with claim 6, wherein the 3D models are obtained by a method selected from a group consisting of computed tomography, magnetic resonance imaging, reconstruction from 2D biplane images biplane and ultrasound images.

8. A system for visually representing the kinematics of a joint of a patient in real-time, comprising:
   an input/output interface configured to receive characteristics of a measured movement of the joint of the patient in real-time;
   a display;
   a processor in communication with the input/output interface and the display, the processor having an associated memory having stored therein processor executable instructions which when executed cause the processor to:
      compute at least one kinematic object vector using specific morphology of structures of the joint of the patient and the characteristics of the measured movement of the joint of the patient in real-time;
      provide to the display a 3D representation of the structures of the joint of the patient based on the specific morphology of the structures of the joint of the patient and on the characteristics of measured movement of the joint of the patient;
      link the at least one kinematic object vector with the structures of the joint of the patient; and
      dynamically provide to the display the at least one kinematic object vector in the form of an arrow to be superimposed on the 3D representation of the structures of the joint of the patient in real-time.

9. A system in accordance with claim 8, wherein characteristics of the arrow are indicative of at least one parameter selected from the group consisting of an amplitude, an orientation, a linear component, an angular component, a velocity, an acceleration, an articular contact points, an axe of rotation a rotational vector and a translational vector.

10. A system in accordance with claim 8, wherein the characteristics of the arrow are further indicative of an uncertainty associated with the computing of the at least one kinematic object.

11. A system in accordance with claim 8, wherein the arrow is dynamically displayed in accordance with the displacements of positional sensors affixed to joint structures.

12. A system in accordance with claim 8, wherein the arrow has a length proportional to a total linear displacement, a bend proportional to an angular displacement and a transverse area proportional to an acceleration and/or velocity.

13. A system in accordance with claim 8, wherein the specific morphology of the structures of the joint of the patient is based on 3D models of the specific morphology of bones constituting the joint of the patient.

14. A system in accordance with claim 13, wherein the 3D models are obtained by a method selected from a group consisting of computed tomography, magnetic resonance imaging, reconstruction from 2D biplane images biplane and ultrasound images.

* * * * *